(12) United States Patent
Alary et al.

(10) Patent No.: US 10,842,242 B2
(45) Date of Patent: Nov. 24, 2020

(54) SYSTEM FOR TARGETED APPLICATION OF TOPICAL AGENTS TO AN ISOLATED BODY PART

(71) Applicant: JOHNSON & JOHNSON CONSUMER INC., Skillman, NJ (US)

(72) Inventors: Marc Alary, Skillman, NJ (US); Jan-Joo Liu, Skillman, NJ (US); Erik Lunde, Skillman, NJ (US); Bharat Patel, Skillman, NJ (US); Emanuel Morano, Totowa, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 30 days.

(21) Appl. No.: 15/848,963

(22) Filed: Dec. 20, 2017

(65) Prior Publication Data
US 2018/0206616 A1    Jul. 26, 2018

Related U.S. Application Data

(60) Provisional application No. 62/437,815, filed on Dec. 22, 2016.

(51) Int. Cl.
*A45D 40/30* (2006.01)
*A61K 8/02* (2006.01)
(Continued)

(52) U.S. Cl.
CPC ........... *A45D 40/30* (2013.01); *A45D 44/002* (2013.01); *A61K 8/0212* (2013.01); *A61K 8/368* (2013.01); *A61P 17/10* (2018.01); *A61Q 19/00* (2013.01); *B32B 38/10* (2013.01); *B33Y 80/00* (2014.12); *B44C 3/02* (2013.01); *A61K 2800/87* (2013.01); *B32B 7/06* (2013.01); *B33Y 10/00* (2014.12)

(58) Field of Classification Search
CPC .. A45D 40/30; A45D 44/002; A61K 2800/87; A61K 8/0212; A61K 8/368; A61P 17/10; A61Q 19/00; B33Y 10/00; B33Y 80/00; B32B 7/06; B32B 38/10; B44C 3/02
USPC .......................... 424/493; 156/235, 247, 249
See application file for complete search history.

(56) References Cited

U.S. PATENT DOCUMENTS 9,060,850 B2    6/2015 Young
9,161,606 B1 *  10/2015 Wong .................... A45D 44/002
(Continued)

FOREIGN PATENT DOCUMENTS

EP    2571395 A     3/2013
EP    2648569 B    10/2013
(Continued)

OTHER PUBLICATIONS

English translation of abstract for WO2006046658.*
(Continued)

*Primary Examiner* — Sonya M Sengupta

(57) ABSTRACT

A system includes an applicator mask having an applicator surface having a three-dimensional shape corresponding to the isolated body part; and at least one membrane releasably disposed on the applicator surface and having an outer surface in facing relation with the applicator surface and inner adhesive surface opposite thereof. The membrane includes one or more benefit agents disposed in one or more treatment zones.

5 Claims, 5 Drawing Sheets

(51) Int. Cl.
*A61K 8/368* (2006.01)
*A61P 17/10* (2006.01)
*A61Q 19/00* (2006.01)
*A45D 44/00* (2006.01)
*B33Y 80/00* (2015.01)
*B33Y 10/00* (2015.01)
*B32B 38/10* (2006.01)
*B44C 3/02* (2006.01)
*B32B 7/06* (2019.01)

(56) References Cited

U.S. PATENT DOCUMENTS

| | | | | |
|---|---|---|---|---|
| 10,004,319 | B2* | 6/2018 | Wong | A45D 44/002 |
| 2003/0044599 | A1* | 3/2003 | Sugii | A61K 8/0208 |
| | | | | 428/343 |
| 2006/0104931 | A1* | 5/2006 | Fukutome | A61K 8/0208 |
| | | | | 424/70.13 |
| 2006/0121097 | A1* | 6/2006 | Lodge | A45D 44/002 |
| | | | | 424/443 |
| 2009/0280150 | A1* | 11/2009 | Kamen | A45D 34/04 |
| | | | | 424/401 |
| 2009/0316965 | A1* | 12/2009 | Mailling | A43D 1/025 |
| | | | | 382/128 |
| 2010/0068247 | A1 | 3/2010 | Mou et al. | |
| 2011/0167571 | A1* | 7/2011 | Yoon | A61K 8/732 |
| | | | | 8/405 |
| 2012/0192884 | A1* | 8/2012 | Nasu | A45D 44/002 |
| | | | | 132/200 |
| 2014/0146190 | A1 | 5/2014 | Mohammadi et al. | |
| 2015/0238352 | A1 | 8/2015 | Young | |
| 2015/0273170 | A1* | 10/2015 | Bachelder | A61M 16/0616 |
| | | | | 128/205.25 |
| 2016/0000208 | A1* | 1/2016 | Wong | A45D 44/002 |
| | | | | 132/320 |
| 2019/0192389 | A1* | 6/2019 | Shinoda | A61K 8/0233 |
| 2019/0254937 | A1* | 8/2019 | Laghi | A61K 8/0208 |

FOREIGN PATENT DOCUMENTS

| | | | | |
|---|---|---|---|---|
| EP | 2962598 A | 1/2016 | | |
| KR | 2015076765 A | 7/2015 | | |
| KR | 20150076765 A | * 7/2015 | | |
| WO | WO-2006046658 A1 | * 5/2006 | | A45D 44/002 |
| WO | WO 2014/151324 A | 9/2014 | | |
| WO | WO 2016/053682 A | 4/2016 | | |

OTHER PUBLICATIONS

Written Opinion for PCT/US2017/067793.*
ISR for PCT/US2017/067793.*
Mintel Database, Avon Clearskin Blemish Clearing Peel-Off Mask, Oct. 2012.
Mintel Database, L'Oreal Demo-Expertise Pure Zone Facial Mask, Apr. 2012.
Mintel Database, Pond's White Beauty Peel-off Instant Brightening Mask, Feb. 2012.
Mintel Database, Yves Rocher Cuidados de Instituto Vegetal Purity Peel-Off Mask with Mint extract, Jun. 2012.

* cited by examiner

SYSTEM FOR TARGETED APPLICATION OF TOPICAL AGENTS TO AN ISOLATED BODY PART

CROSS-REFERENCE TO RELATED APPLICATIONS

This application claims the benefit of U.S. provisional application 62/437,815 filed on Dec. 22, 2016.

FIELD OF THE INVENTION

The present invention relates to a system for targeted application of topical agents to an isolated body part. More specifically, the present invention is directed to a system for treating common consumer skin flaws including an applicator mask having a three-dimensional shape corresponding to the isolated body part used in combination with an active substance containing membrane structure for delivery of active substance in the membrane structure to the skin of the consumer, and methods of using the system.

BACKGROUND OF THE INVENTION

Ageless, flawless, youthful skin appearance is the desire of many people around the world. Common skin flaws include: acne, age spots, birthmarks, dry skin, eczema, hyperpigmentation, large pores, moles, psoriasis, rosacea, scars, sun spots, under eye circles, warts, and wrinkles.

Consumers are always looking for the next product or treatment that will treat these flaws and keep them younger looking, and in particular, safer and more effective methods and products for rejuvenating the skin. There are many known formulation in the form of creams, lotions, powders and oils which consumers apply to their face, hands, feet and bodies specifically targeting the various common skin flaws. Many have active substances, or benefit agents for use in treating the flaws.

Commercial available two-dimensional products, such as facial mask sheet or cloth like materials are homogeneous structures which are worn across the entire face. Such sheets are also known for use on other isolated body parts such as arms, hands, legs, or feet. These types of products are not personalized for consumers in terms of treatments, size and configuration to perfectly fit a consumer's anatomy and treat a consumer's personal needs. For instance, in facial treatments, the same facial treatment ingredient is applied to chin, cheeks and to nose, despite significant differences among the skin conditions found on the chin, cheek and nose in different patients.

In addition, since the above-mentioned sheets are formed in two dimensions, it is impossible to precisely conform it to three-dimensional profile of human face and therefore it could not precisely deliver target treatments for such as red spots, acnes, pigmentation, fine line wrinkles, etc. In addition, the application of conventional facial mask is often in wet form. It is easy to fall during wearing.

In summary, two-dimensional skin care sheet-like products are not able to precisely deliver target the delivery of benefit agents to isolated body parts of the human body such as face, such as arms, hands, legs, or feet. They are not personalized for consumers in terms of treatments, size and configuration to perfectly fit a consumer's anatomy and treat a consumer's personal needs. Needed to avoid these limitations are systems for targeted application of topical agents to an isolated body part, as well as methods of using the system.

SUMMARY OF THE INVENTION

Surprisingly, we have found that carefully targeted application of topical agents to an isolated body part can be accurately achieved using a system including an applicator mask having an applicator surface having a three dimensional shape corresponding to the isolated body part; and at least one membrane releasably disposed on the applicator surface and having an outer surface in facing relation with the applicator surface and inner adhesive surface opposite thereof. The membrane includes one or more benefit agents disposed in one or more treatment zones.

In addition we have identified a method for targeted application of topical agents to an isolated body part comprising the steps of capturing an image of the isolated body part, transforming the image data to mathematical model of the geometry of the isolated body part, forming an applicator mask having an applicator surface having a three dimensional shape corresponding to the isolated body part, forming a releasable membrane on the applicator surface of the applicator mask comprising one or more benefit agents disposed in one or more treatment zones of the applicator, where the adhesion of the membrane to the isolated body part is greater than the adhesion of the membrane to the applicator surface, disposing the applicator mask on the isolated body part so that the releasable membrane is in contact with the isolated body part, and removing the applicator mask from the isolated body part so that the membrane remains in contact with the isolated body part.

DETAILED DESCRIPTION OF THE INVENTION

The present invention relates to systems for the administration of active substances to the skin of a consumer and methods employing the system. The following description is presented to enable one of ordinary skill in the art to make and use the invention. Various modifications to the embodiments and the generic principles and features described herein will be readily apparent to those skilled in the art. Thus, the present invention is not intended to be limited to the embodiments shown, but is to be accorded the widest scope consistent with the features described herein.

As used herein the specification and the claims, the term "topical" and variants thereof mean of or applied to an isolated part of the body. This includes, without limitation skin, mucosa, and enamel.

As used herein, "benefit agent" means an ingredient or material that provides a benefit, e.g., improves, relieves, reduces, or treats symptoms or conditions of the skin, ether cosmetic or therapeutic.

The method for treating common consumer skin flaws described herein uses an applicator having a three-dimensional shape corresponding to the isolated body part used in combination with a benefit agent containing membrane structure for delivery of benefiting agent substance in the membrane structure to the skin of the consumer, and methods of using the system. The three-dimensional conformal applicator has varying personalized area-specific treatment zones to enable the treatment application more effectively. With a three-dimensional conformal applicator matched to the individual user's body part profile as physical guides, the application becomes easier and more effective, and can help in locating specific target zones to the precise area for applications.

Figure 1:
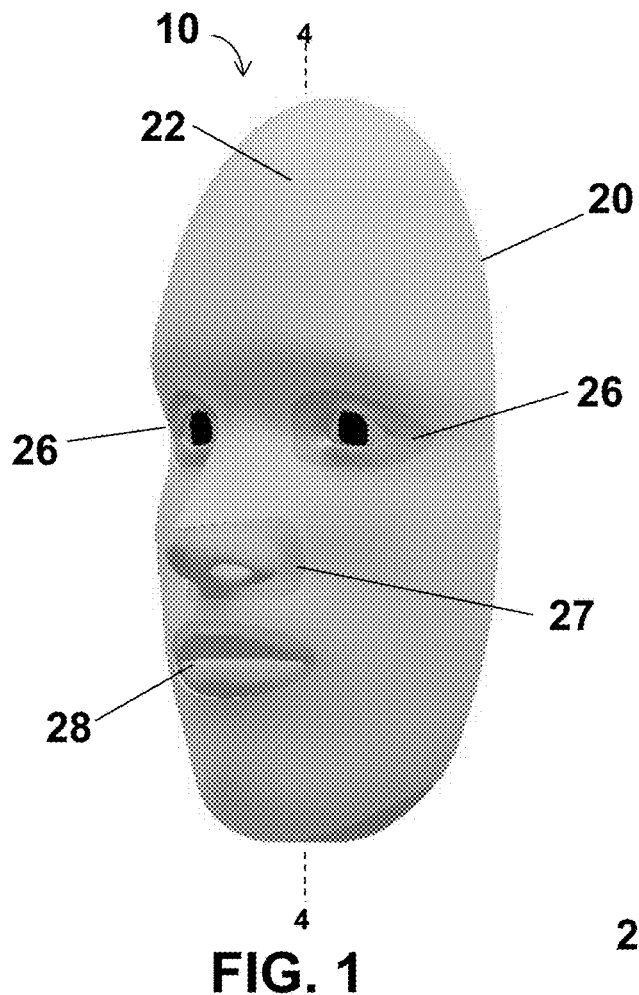
FIG. 1 is a front perspective view of a first face embodiment of the system of the present invention.
Figure 2:
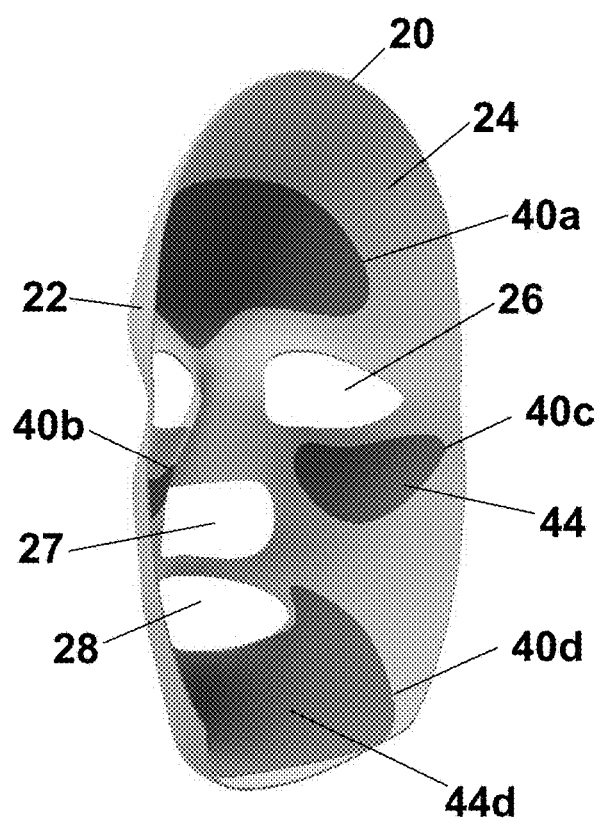
FIG. 2 is a rear perspective view of the first face embodiment of the system of FIG. 1.
Figure 3:
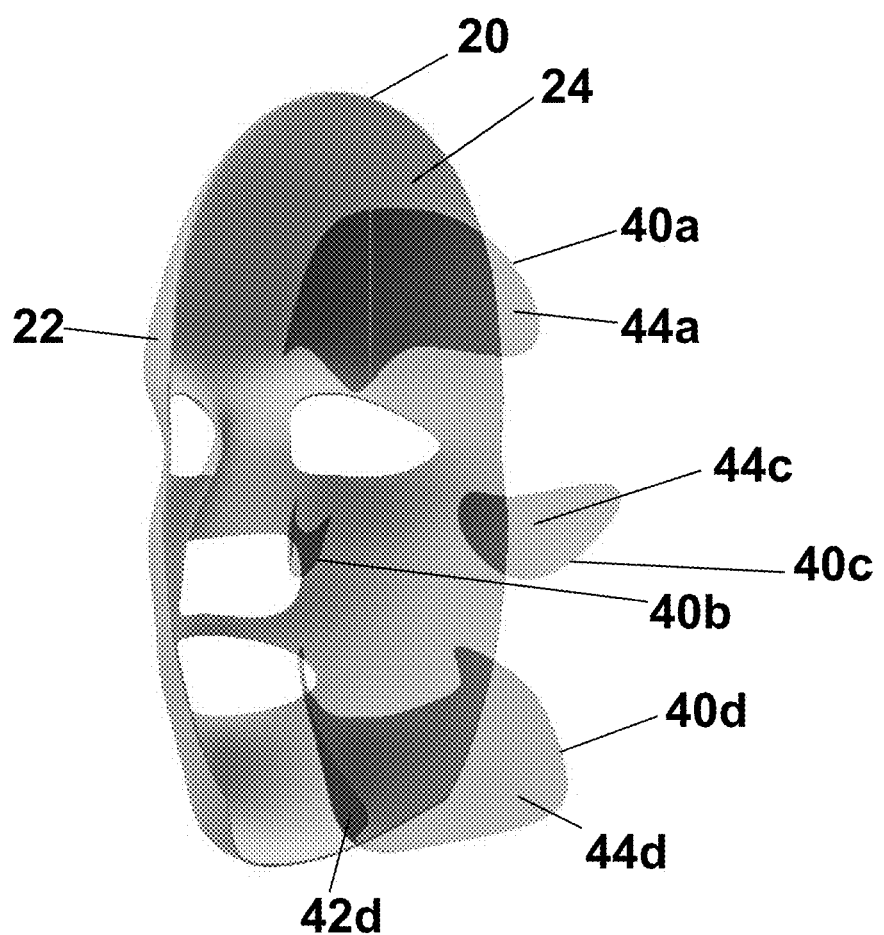
FIG. 3 is a rear exploded view of the first face embodiment of the system of FIG. 1.

Referring to the drawings, FIGS. 1 and 2 are front and rear perspective views, respectively, of a first embodiment of a skin treatment system 10 which may be used in the present invention. FIG. 3 is a rear exploded view of system 10. Skin treatment system 10 includes applicator 20 having a first surface 22, and a second surface 24. In this embodiment, applicator 20 is shown as a facial mask.

Applicator 20 in this embodiment has eye openings 26, a nose opening 27, and a mouth opening 28, and is sized to cover the full face of the user. It is important to note that in other facial mask type embodiments, applicator 20 may be sized to partially cover the face of the user, and may be without any of the openings described above.

Disposed on second surface 24 of applicator 20 are active membranes 40a, 40b, 40c, and 40d. This plurality of active membranes is releasably disposed on second surface 24 of applicator 20, and contain one or more benefit agents. Active membranes 40a, 40b, 40c, and 40d have first surfaces and second surfaces. FIG. 3 shows first surface 42d of active membrane 40d, as well as second surfaces 44a, 44c, and 44d of active membranes 40a, 40c, and 40d, respectively. The bond between applicator 20 and active membranes 40a, 40b, 40c, and 40d occur between second surface 24 of applicator 20 and first surfaces of the active membranes.

Active membrane 40a is located in the forehead region of facial mask applicator 20, while active membranes 40b and 40c are located in the cheek region of facial mask applicator 20 and active membrane 40d is located in the chin region of facial mask applicator 20. Although the embodiment shown has an applicator 20 with four releasably disposed active membranes (40a, 40b, 40c, and 40d), other embodiments may have more or less releasably disposed membranes. Some embodiments may have one or more active membrane, or two or more active membranes, or four or more active membranes, or six or more active membranes, or eight or more active membranes, or twelve or more active membranes. The number and location of active membranes 40 depend on the common consumer skin flaw(s) being treated.

Active membranes 40 contain one or more benefit agents. In some embodiments, active membranes may contain two, three, four, or more benefit agents. Also, if there are two or more active membranes, each active membrane may contain the same beneficial agent(s), or each active membrane may contain different beneficial agent(s). In some embodiments, individual active membranes may contain more than one benefit agent. Also, different regions of the active membrane may contain different active agents, or may contain a gradient of active agent from one region to another. For example, the active agent may have a lower concentration proximate the edges to "feather" the treatment effect.

Active membranes 40 may also have a variety of shapes, depending on the location of skin treatment. Possible shapes of the footprint left by active membranes 40 include, but are not limited to, squares, rectangles, triangles, circles, ovals, kidneys, stars, crosses, characters, etc. The corners of such shapes, if any, may be angular or curved to reduce potential lift/removal points. The zone of the treatment could be greater than about 1,000 $cm^2$, about 1,000 $cm^2$, or about 100 $cm^2$, or about 10 $cm^2$, or about 1 $cm^2$, or less than 1 $cm^2$.

Figure 4:
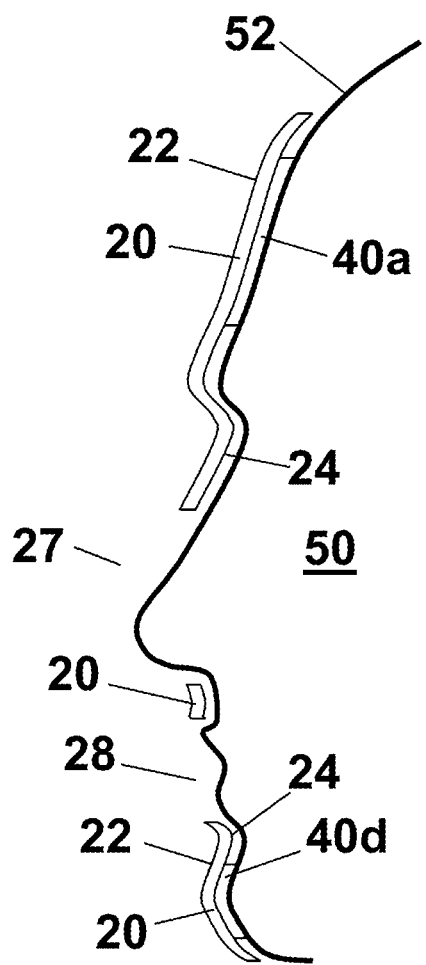
FIG. 4. is a side cross sectional view of the system of FIG. 1 along the 4-4 plane disposed on a user's face prior to removal of the applicator portion of the system.
Figure 5:
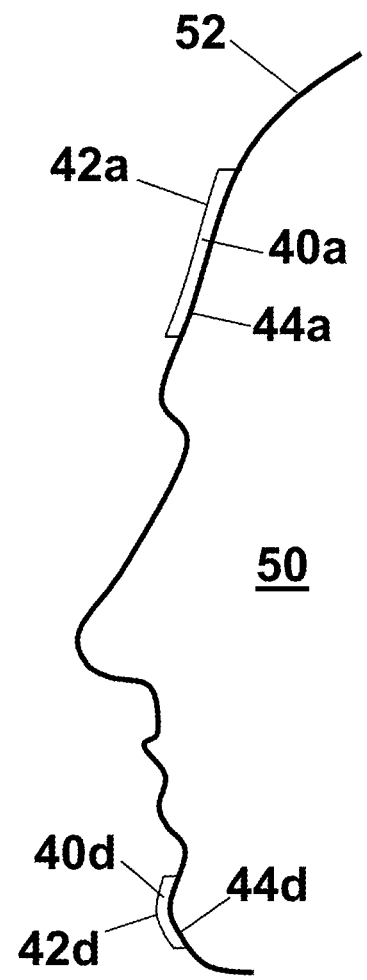
FIG. 5. is a side cross sectional view of the system of FIG. 1 along the 4-4 plane disposed on a user's face after removal of the applicator portion of the system.

In use, skin treatment system 10 of the present invention will be disposed on the user's skin, and the applicator portion will be removed therefrom. FIGS. 4 and 5 are side cross sectional views of system 10 along the 4-4 plane of FIG. 1 disposed on a user's face prior to, as well as after, removal of the applicator portion of the system. The figures show sections of applicator 20 with first surface 22 and second surface 24, active membranes 40a and 40d with first surfaces 42a, 42d and second surfaces 44a, 44d, and user's face 50 with face surface 52. The sections of applicator 20 seen in the figures are those above nose opening 27, between nose opening 27 and mouth opening 28, and below mouth opening 28.

FIG. 4 shows that when skin treatment system 10 is disposed on the user's face 50, second surfaces 44a, 44d of active membranes 40a and 40d are in contact with surface 52 of face 50. Second surface 24 of applicator 20 remains in contact with first surfaces 42a, 42d of active membranes 40a and 40d until removed by the user. Removal of applicator 20 by the user results in the structure shown in FIG. 5. When applicator 20 is removed, second surfaces 44a, 44d of active membranes 40a and 40d remains in contact with surface 52 of face 50 at the treatment zone.

In accordance with a more particular aspect of the present invention, second surface 24 of applicator 20 releasably attaches to first surfaces 42a, 42d of active membranes 40a and 40d. The attachment strength of applicator 20 to active membranes 40a and 40d is less than the adhesive strength of membranes 40a and 40d to skin. So, when applicator 20 is removed by the user, active membranes 40a and 40d remains adhered to skin 50. In some embodiments, membranes 40a and 40d are held in place by spot application of adhesive.

In some embodiments, the shear strength of applicator 20 to active membranes 40a and 40d is less than the shear strength of membranes 40a and 40d to skin. So, when applicator 20 is removed by the user, active membranes 40a and 40d remains adhered to skin 50.

In some embodiments, a plurality of releasable membranes is formed in a stack on the applicator surface of the applicator mask, each releasable membrane comprising one or more benefit agents disposed in one or more treatment zones of the applicator. The adhesion of the membrane to the isolated body part is greater than the adhesion of the membrane to the applicator surface and to an adjacent membrane in the stack.

Figure 6:
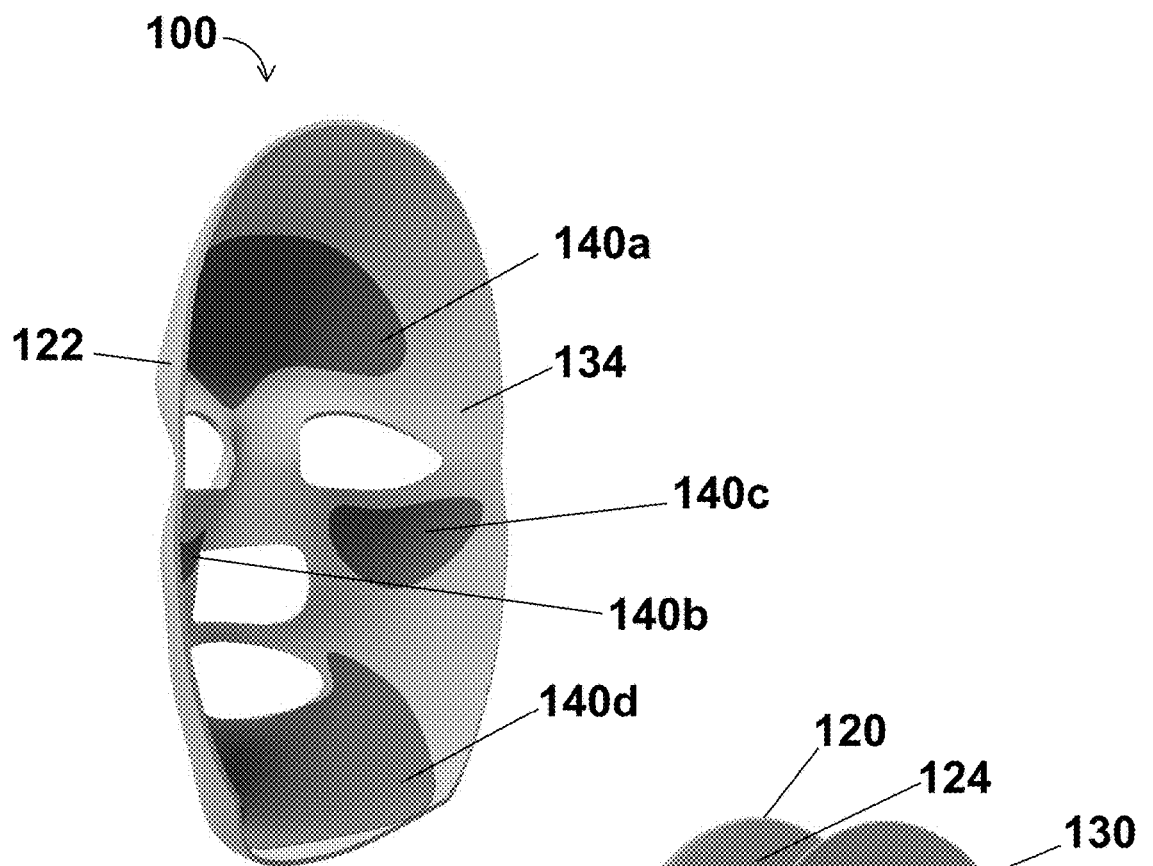
FIG. 6. is a rear perspective view of a second face embodiment of the system of the present invention.
Figure 7:
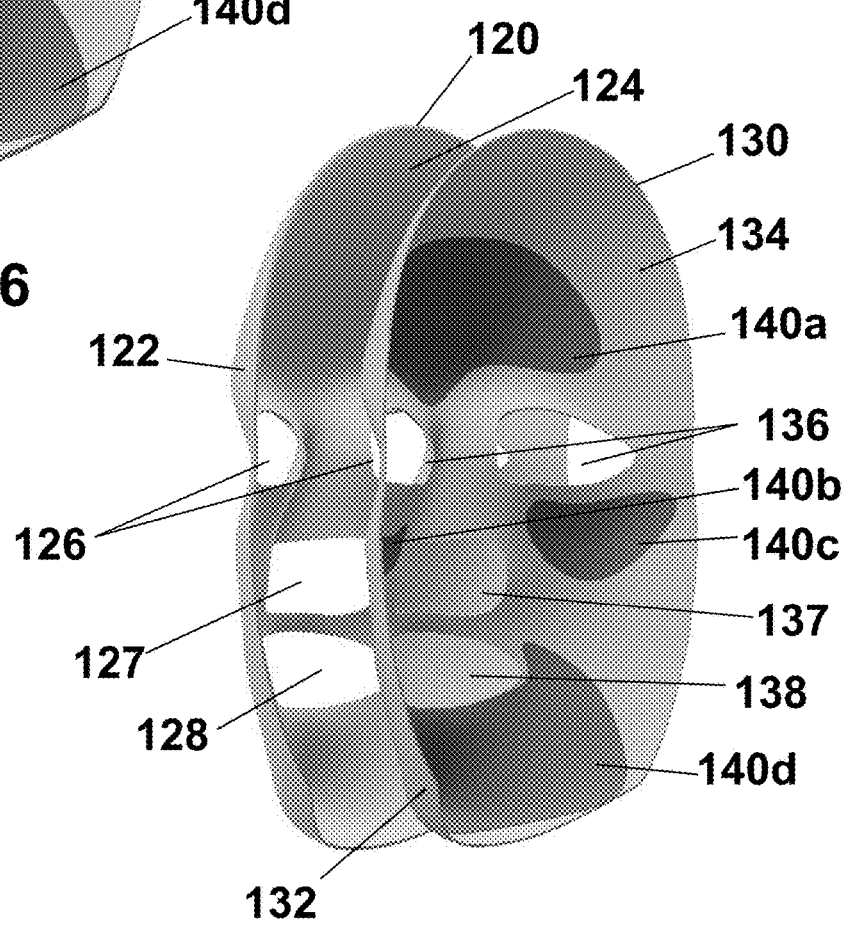
FIG. 7. is a rear exploded view of the second face embodiment of the system of FIG. 7.

FIGS. 6 and 7 are views of a second face embodiment of the system 100 of the present invention. FIG. 6 is a rear perspective, while FIG. 7 is a rear exploded view of system 100. The skin treatment system 100 includes applicator 120 having a first surface 122, and a second surface 124. In this embodiment, applicator 120 is shown as a facial mask.

Applicator 120 in this embodiment has eye openings 126, a nose opening 127, and a mouth opening 128, and is sized to cover the full face of the user. It is important to note that in other facial mask type embodiments, applicator 120 may be sized to partially cover the face of the user, and may be without any of the openings described above.

Disposed on second surface 124 of applicator 120 is membrane 130, which is releasably disposed on second surface 124 of applicator 120. Membrane 130 has a first surface 132, and a second surface 134, and has active regions 140*a*, 140*b*, 140*c*, and 140*d* which contain one or more benefit agents. The bond between applicator 120 and membrane 130 occurs between second surface 124 of applicator 120 and first surface 132 of the membrane 130.

Membrane 130 in this embodiment has eye openings 136, a nose opening 137, and a mouth opening 138, and is sized to cover the full face of the user. It is important to note that in other embodiments, membrane 130 may be sized to partially cover the face of the user, and may be without any of the openings described above.

In this embodiment, active region 140*a* is located in the forehead region of facial mask applicator 120, while active regions 140*b* and 140*c* are located in the cheek region of facial mask applicator 120 and active region 140*d* is located in the chin region of facial mask applicator 120. Although the embodiment shown has an applicator 120 having releasably disposed membrane 130 with four active regions (140*a*, 140*b*, 140*c*, and 140*d*), other embodiments may have membranes 130 with more or less active regions. Some embodiments may have one or more active regions, or two or more active regions, or four or more active regions, or six or more active regions, or eight or more active regions, or twelve or more active regions. The number and location of the active regions 140 depend on the common consumer skin flaw(s) being treated.

As mentioned earlier, active regions 140 contain one or more benefit agents. In some embodiments, active regions may contain two, three, four, or more benefit agents. Also, if there are two or more active regions, each active region may contain the same beneficial agent(s), or each active region may contain different beneficial agent(s).

Active regions 140 may also have a variety of shapes, depending on the location of skin treatment. Possible shapes of the active regions 140 include, but are not limited to, squares, rectangles, triangles, circles, ovals, kidneys, stars, crosses, characters, etc. The zone of the treatment could be greater than about 1,000 $cm^2$, about 1,000 $cm^2$, or about 100 $cm^2$, or about 10 $cm^2$, or about 1 $cm^2$, or less than 1 $cm^2$.

In accordance with a more particular aspect of the present invention, second surface 124 of applicator 120 releasably attaches to first surface 132 of membrane 130. The attachment strength of applicator 120 to membrane 130 is less than the adhesive strength of membrane 130 to skin. So, when applicator 120 is removed by the user, membrane 130 remains adhered to the skin at the location of the treatment zone.

Figure 8:
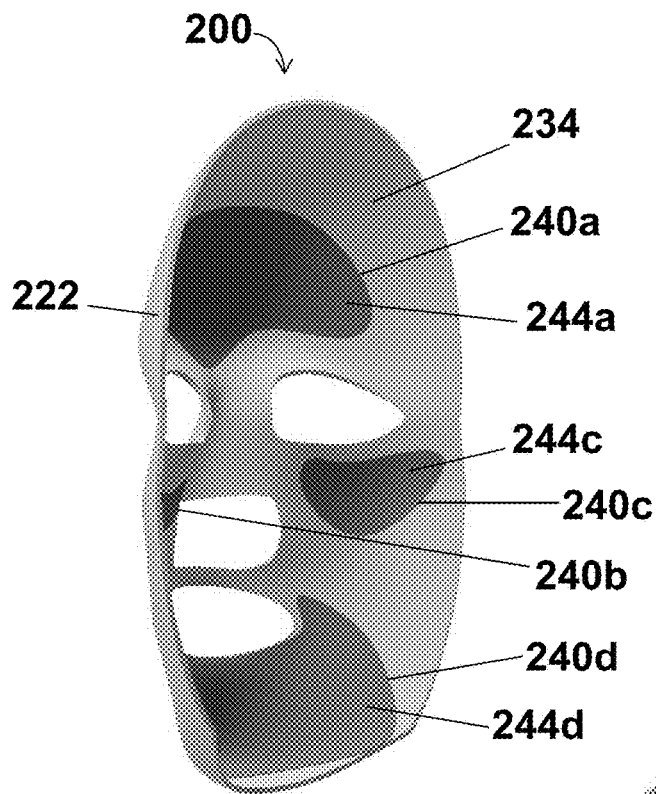
FIG. 8. is a rear perspective view of a third face embodiment of the system of the present invention.
Figure 9:
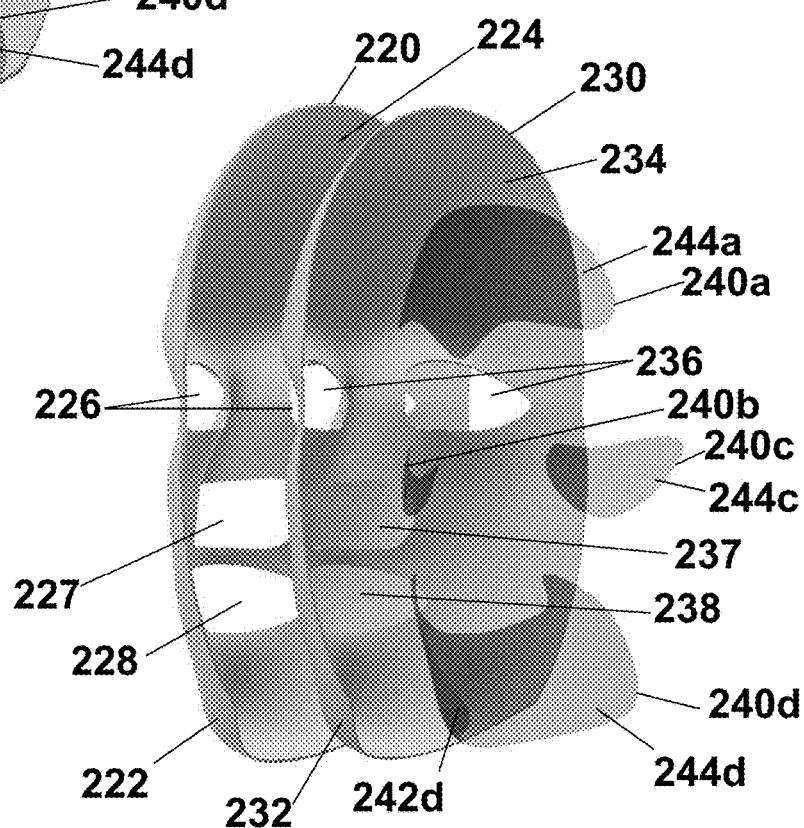
FIG. 9 is a rear exploded view of the third face embodiment of the system of FIG. 8.

FIGS. 8 and 9 are views of a third face embodiment of the system 200 of the present invention. FIG. 8 is a rear perspective, while FIG. 9 is a rear exploded view of system 200. The skin treatment system 200 includes applicator 220 having a first surface 222, and a second surface 224. In this embodiment, applicator 220 is shown as a facial mask.

Applicator 220 in this embodiment has eye openings 226, a nose opening 227, and a mouth opening 228, and is sized to cover the full face of the user. It is important to note that in other facial mask type embodiments, applicator 220 may be sized to partially cover the face of the user, and may be without any of the openings described above.

Disposed on second surface 224 of applicator 220 is membrane 230, which is releasably disposed on second surface 224 of applicator 220. Membrane 230 has a first surface 232, and a second surface 234. The bond between applicator 220 and membrane 230 occurs between second surface 224 of applicator 220 and first surface 232 of membrane 230.

Membrane 230 in this embodiment has eye openings 236, a nose opening 237, and a mouth opening 238, and is sized to cover the full face of the user. It is important to note that in other embodiments, membrane 230 may be sized to partially cover the face of the user, and may be without any of the openings described above.

Disposed on second surface 234 of membrane 230 are active membranes 240*a*, 240*b*, 240*c*, and 240*d*. In some embodiments, these active membranes are releasably disposed on second surface 234 of membrane 230, and contain one or more benefit agents. Active membranes 240*a*, 240*b*, 240*c*, and 240*d* have first surfaces and second surfaces. FIG. 9 shows first surface 242*d* of membrane 240*d*, as well as second surfaces 244*a*, 244*c*, and 244*d* of active membranes 240*a*, 240*c*, and 240*d*, respectively. The bond between membrane 230 and active membranes 240*a*, 240*c*, and 240*d* occur between second surface 234 of membrane 230 and first surfaces of the membranes.

In this embodiment, active membrane 240*a* is located in the forehead region of membrane 230, while active membranes 240*b* and 240*c* are located in the cheek region of membrane 230 and active membrane 240*d* is located in the chin region of membrane 230. Although the embodiment shown has a membrane 230 with four active membranes (240*a*, 240*b*, 240*c*, and 240*d*), other embodiments may have more or less active membranes. Some embodiments may have one or more active membranes, or two or more active membranes, or four or more active membranes, or six or more active membranes, or eight or more active membranes, or twelve or more active membranes. The number and location of the active membranes 240 depend on the common consumer skin flaw(s) being treated.

As mentioned earlier, active membranes 240 contain one or more benefit agents. In some embodiments, membranes may contain two, three, four, or more benefit agents. Also, if there are two or more active membranes, each active membrane may contain the same beneficial agent(s), or each active membrane may contain different beneficial agent(s).

Active membranes 240 may also have a variety of shapes, depending on the location of skin treatment. Possible shapes of the active membranes 240 include, but are not limited to, squares, rectangles, triangles, circles, ovals, kidneys, stars, crosses, characters, etc. The zone of the treatment could be greater than about 1,000 $cm^2$, about 1,000 $cm^2$, or about 100 $cm^2$, or about 10 $cm^2$, or about 1 $cm^2$, or less than 1 $cm^2$.

In accordance with a more particular aspect of the present invention, second surface 224 of applicator 220 releasably attaches to first surface 232 of membrane 230. The attachment strength of applicator 220 to membrane 230 is less than the adhesive strength of membrane 230 to skin. So, when applicator 220 is removed by the user, membrane 230 remains adhered to the skin at the location of the treatment zone.

It is important to note that although skin treatment systems 10, 100 and 200 in the embodiments of the present invention use applicators 20, 120 and 220 in the form of a facial mask, skin treatment systems may also be used on other isolated body parts, such as arms, hands, legs, or feet, for example. In these other embodiments, applicators 20, 120 and 220 will be shaped as appropriate for other isolated body parts.

Applicators 20, 120 and 220 are made of a flexible, biocompatible material which is capable of forming to the site of treatment on the skin of the consumer. There are numerous flexible, biocompatible material materials which may be used to form applicators. These materials include, but are not limited to: polyolefins like poly(ethylene) (PE) or poly(propylene) (PP); poly(tetrafluoroethylene) (PTFE); poly(vinyl chloride) (PVC); silicones like poly(dimethyl silane) (PDMS); polyacylates like poly(methyl methacrylate) (PMMA) or poly(hydroxyethyl methacrylate) (pHEMA); polyesters like poly(ethylene terephthalate) (PET), poly(glycolic acid) (PGA), poly-L-lactic acid (PLA), or polydioxanone (PDO); polyethers like polyether ether ketone (PEEK) or polyether sulfone (PES); polyamide (Nylon); or polyurethane (PU), polycaprolactone, or combinations of the above. The method of forming applicator 20 will be discussed later.

In accordance with a more particular aspect of the present invention, the attachment strength of the applicator to the membrane is less than the adhesive strength of the membranes to skin. So, when the applicator is removed by the user, the membrane remains adhered to the skin at the location of treatment zone.

This relative adhesive strength is provided by modifying the material of the applicator, at least on the second surface (24, 124, or 224) of the applicator (the surface that is directed toward the skin during use), or the first surface (42, 132, or 232) of the membrane (the surface that is directed away from the skin during use). Adding a tackifier to the material in the applicator or the membrane can increase the attachment strength between the two. The attachment strength between the applicator (20, 120 or 220) and the accompanying membrane (40, 130, or 240) is also affected by the surface texture of the surface of the applicator in contact with the membrane. Imparting a texture, such as a plurality of parallel grooves, a bead-blasted texture, and the like, can increase the attachment strength therebetween.

Membranes 40, 130, and 240 of the present invention are provided in forms that are comfortable to wear and readily removable after remaining in place for an extended period of time, e.g., at least half an hour, or at least one hour, or at least about six (6) to eight (8) hours, or at least about twelve (12) hours, or about twenty-four (24) hours, if desired. Membranes 40, 130, and 240 are readily removable either by low adhesion to skin, or upon application of water thereto. By readily removable upon application of water thereto, it is meant that the membrane structure may dissolve or disintegrate upon application of water to the membrane structure, such that it may be removed from the skin without scrubbing, or the like. In some embodiments, the membranes may lose adhesion over time and fall off of the sight. Membranes 40, 130, and 240 preferably are a topically-applied skin care film, patch, applique, etc. (hereinafter "film structure" for the sake of convenience, without intent to limit) that preferably is relatively flexible.

Membranes 40, 130, and 240 of the present invention preferably are relatively thin and flexible, as described in further detail below, so that they preferably readily conform to the user's skin and are comfortable to wear, both because of the flexibility and conformability, as well as from the thinness. Membranes 40, 130, and 240 of the present invention intended for extended wear preferably are also formed to be aesthetically elegant without either peeling, wrinkling, cracking, or appearing greasy or tacky, or otherwise unpleasant or unsightly in nature. Membranes 40, 130, and 240 preferably are formed with sufficient rigidity and integrity to be able to withstand normal use when on the skin. For instance, membranes 40, 130, and 240 of the invention preferably are formed with sufficient strength to stay intact on the skin when exposed to normal external forces that the skin may experience, e.g., rubbing of clothing, pillow, etc.

If desired, membranes 40, 130, and 240 of the present invention may be formed to have structural integrity. As used herein, structural integrity is to be understood as the physical capability of the membranes to maintain a substantially monolithic form or structure and to resist tearing or fracture while being manipulated independent of the applicator.

It will be appreciated that structural integrity of membranes 40, 130, and 240 of the present invention preferably also contributes to the membranes' ability to remain intact during manipulation and use, and to conform to the contours of the application site to which they are applied, as discussed in further detail below. For instance, it is desirable that each membrane have sufficient structural integrity so that the membrane does not readily tear when manipulated, worn, or otherwise used. It will be appreciated that selection of one or more film formers that contribute to a product's ability to achieve a pliable, cohesive, and continuous covering on an application site such as skin, is one manner of achieving the desired structural integrity of a membrane of the present invention. In some embodiments, selection of one or more plasticizers for producing or promoting plasticity and flexibility and reducing brittleness, is another manner of achieving the desired structural integrity of a membrane of the present invention.

The structural integrity of membranes 40, 130, and 240 of the present invention typically may be correlated with the tensile strength or modulus and thickness of their structure. In connection with the present invention, structural integrity typically increases as thickness and yield strength increase. However, such properties must be balanced with their effect on whether the membrane is comfortable to be worn, as discussed in further detail below. Tensile strength contributes to the structural integrity of membranes 40, 130, and 240 used in accordance with principles of the present invention for such purposes as handling and/or removing the membranes 40, 130, and 240 from the skin. Tensile strength affects, inter alia, whether the membrane resists being fractured when being handled and/or removed from the skin. For instance, membranes 40, 130, and 240 of the present invention preferably have an elastic modulus of about 500 psi to about 10,000 psi. An elastic modulus of about 2,500 psi has been found in one embodiment to provide the desired stiffness to be comfortable during use. Typical samples with a ¾ inch (1.905 cm) width and a 0.1 mm thickness have a rupture-strength of about 2 lbf (pound force), although it will be appreciated that a useful range of rupture strengths is from about 0.5 lbf to about 5 lbf. The membrane's adhesion values are preferably between 225 gms/25 mm to 1500 gms/25 mm (8-50 oz/in). However, in some circumstances that will be recognized by the person of ordinary skill in the art, the adhesion values may be as large as 3000 gms/25 mm (100 oz/in). The shear values for the membrane are preferably greater than 250-500 minutes on a PSTC-107 (ASTM D3654)—procedure A.

The adhesion between the applicator and the membrane is preferably about 2-3 oz/in or 10-20% lower adhesion than the adhesion between the membrane and the topical surface to which it is applied (whichever is higher). If membranes are stacked in the applicator, a similar relation between adhesion of the body-contacting membrane to the topical surface and the adhesion of the body-contacting membrane to an adjacent membrane can be used.

The thickness of the membrane also affects structural integrity. For instance, the thickness of a membrane of the present invention may be between about 0.05 mm to about 2 mm, and preferably between about 0.05 mm and 0.3 mm. A thickness of approximately 0.1 mm has been found to provide the desired mechanical properties for handling, applying, and ultimately removing the membrane, such that the membrane maintains its structural integrity throughout such use, as well as while being worn on a given application site, as discussed in further detail below.

In accordance with one aspect of the present invention, membranes 40, 130, and 240 of the present invention are self-adhesive, i.e., the membrane adheres to a user's skin upon contact with the skin, preferably without additional steps, such as addition of another composition, such as water.

In one embodiment, water soluble bio adhesive polymers can be used for enhancing skin adhesive property. Examples useful for the invention include, but are not limited to, cellulose and its derivatives, polyvinyl pyrrolidone, water soluble celluloses, polyvinyl alcohol, ethylene maleic anhydride copolymer, methylvinyl ether maleic anhydride copolymer, acrylic acid copolymers, anionic polymers of methacrylic acid and methacrylate, cationic polymers with dimethyl-aminoethyl ammonium functional groups, polyethylene oxides, water soluble polyamide or polyester, polyethylene glycol, water soluble acrylic polymers, water soluble polyesters, hydroxyalkyl starches, casein, gelatin, solubilized proteins, polyacrylamide, polyamines, polyquaternium amines, styrene maleic anhydride resins, polyethylene amines, The water soluble carbohydrate can form hydrogen or covalent bonding to the water soluble or hydrophilic polymer in the membrane.

In accordance with one aspect of the present invention, the adhesive quality of membranes 40, 130, and 240 of the present invention are preferably capable of fixing the membrane to the skin of a user for an extended period of time, as discussed herein above, without irritating the skin. Preferably, the membrane is capable of adhering to the application site for as long as reasonable and/or indicated to have a membrane in place at such site. Thus, an upper temporal limit to adhesion time is not important, since the user or wearer typically will want to remove the membrane before the membrane would naturally wear off of the application site on its own. In embodiments where membranes 40, 130, and 240 are readily removable upon application of water thereto, the amount of time a membrane of the present invention is to adhere to a given application site is dictated by the amount of time the application area can withstand not being exposed to water. For instance, it will be appreciated that some surgical sites are not to be exposed to water for extended periods of time, such as several days. Membranes for application to such sites should accordingly be capable of adhering to such site for so long as the site is not exposed to water, if desired. As may be appreciated, the adhesive preferably is selected for application onto a skin surface which typically is not considered to be moist, in contrast with mucosal tissue. It will be appreciated that by being capable of adhering to the user's skin, the membrane simply is capable of adhering, but need not necessarily adhere if such property is not desired or unnecessary for a particular application.

Because membranes 40, 130, and 240 of the present invention preferably are formed to remain adhered to the application site for an extended period of time, as described above, non skin-contacting surfaces (first surfaces 42, 132, and 244 of membranes 40, 130, and 240, respectively), preferably have desirable properties and features to facilitate such an intended use of the membrane. For instance, because a membrane is designed to adhere to an application site, if the membrane is designed to adhere to an application site for an extended period of time, then an adhesive outwardly-facing surface may unintentionally or inadvertently adhere to another surface or object during use of the membrane. Such unintentional or inadvertent occurrence may cause the membrane to become dislodged, or, worse, disengaged (partially or even fully) from the application site. Moreover, it will be appreciated that an adhesive material typically attracts dust or dirt or other debris, which would likely be considered by the wearer to be unsightly and undesirable. Accordingly, it is preferable that non skin-contacting surfaces (first surfaces 42, 132, and 244 of membranes 40, 130, and 240, respectively) of the present invention are non-tacky; not adhesive, and create low or no static when rubbed. Thus, for membranes 40, 130, and 240 of the present invention, to remain adhered to an application site for an extended period of time, preferably have first surfaces 42, 132, and 244 that are non-tacky; non-adhesive.

If first surfaces 42, 132, and 244 rub against or are rubbed by something or otherwise contacts or is contacted by another surface or Membranes 40, 130, and 240, the membranes 40, 130, and 240 should not adhere to such surface or membrane.

Membranes 40, 130, and 240 may be tinted or pigmented to match the skin tone of the user so to be aesthetically pleasing, or at least not unaesthetic or unsightly, when worn.

Membranes 40, 130, and 240 may be formed to be clear to be discrete in situ. Further properties may be selected to render membranes 40, 130, and 240 of the present invention visually discrete when in situ so that if the membrane is worn during the day its noticeability is minimized as much as possible. For instance, the thinner the membrane is, the less visible the structure typically is. In addition, or alternatively, the color, texture (e.g., rough, slick, smooth, or otherwise textured such as an "orange peel" surface to match substantially the texture of the skin to which the membrane is applied so that the membrane is not starkly smooth relative to the skin with its natural imperfections), shine (shiny or dull depending on application site), etc., may be modified as desired to facilitate blending in of the membrane with the application site. Because membranes 40, 130, and 240 of the present invention may be configured to be worn for an extended period of time (e.g., more than an hour, such as described above, and/or even overnight), the membrane preferably is formed or configured to be comfortable when worn. A variety of factors (individually or in any combination) may be considered in achieving the desired comfort and level of comfort, including, without limitation, tactile properties, material thickness (affecting not only durability, but also weight on the application site), stiffness and permeability. Tactile properties that may contribute to comfort include smoothness, and/or stickiness of the adhesive used to adhere the membrane structure to a selected application site, etc. Additional tactile properties that may contribute to comfort include softness, smoothness, and texture of the membrane, such as determined by modulus of elasticity and coefficient of friction (rather than merely the aesthetic aspects of such properties).

Thickness affects a variety of additional factors, including stiffness—a stiffer membrane typically being less comfortable than a less stiff membrane. Material properties (a function of the composition of the material, independent of form) as well as structural properties (the form of the membrane) may affect the achievable comfort level of a membrane used in accordance with principles of the present invention when worn by a user. It will be appreciated that all the desired properties for a membrane used in accordance with principles of the present invention must be balanced, wherein some properties complementary, yet others have opposing dimensions. With regard to comfort, it will be appreciated that properties contributing to comfort must be balanced with properties contributing to structural integrity. There are at least three structural properties that affect "comfort": flexibility (about a single, bending direction; generally, flexibility is considered a combination of thickness and flexural modulus), stretchability (in a single axial direction; generally, stretchability is considered a combination of thickness and elastic modulus), and conformability (generally considered a combination of flexibility and physical shape in multiple directions, about complex surface). Comfort may be achieved by minimizing both the thickness and the elastic modulus. It will be appreciated that flexibility and stretchability are both functions of the elastic modulus of the material. More particularly, flexibility generally is dictated by the thickness of the material as well as the flexural modulus. Stretchability is a function of thickness and elastic modulus. When the material is thicker, stiffness increases (which property correlates with comfort) and flexibility and stretchability are reduced, generally adversely impacting comfort. The elastic modulus generally affects how rubbery or brittle a material is, and is tied to comfort because it determines flexibility of the material. Increasing the flexural or elastic modulus of a material makes the material less flexible or stretchable, respectively. Specifically, a higher flexural or elastic modulus results in a stiffer material, so the material consequently is less flexible and less stretchable. Given a constant flexural or elastic modulus, a higher material thickness will make the material less flexible or stretchable. As may be appreciated, comfort may be achieved by minimizing thickness of a given film to the lowest practical limit. The lower limit is dictated by providing enough structure to handle and manipulate the self-supporting adhesive film and to facilitate application and removal of the self-supporting adhesive film. From a material standpoint, the elastic modulus is most strongly linked to comfort. The lower the elastic modulus, the more comfortable the film structure typically is. An elastic modulus of from about 500 psi to about 10,000 psi provides an acceptable degree of comfort for a user, with a more preferred range of elastic modulus of from about 1,000 psi to about 5,000 psi, with a preferred elastic modulus of about 2,500 psi. Conformability, such as the ability to conform to a given site (typically a surface with a complex curvature), not only involves flexibility, in general, but also relates to multidirectional flexibility and stretchability (e.g., so the membrane may stretch if placed over a joint). Conformability generally must be defined in terms of the physical shape or contour of the application site, and is determined with respect to a surface in conjunction with flexibility. A membrane may need to have a particular planar shape to be able to conform to a complex surface. Preferably, a membrane used in accordance with principles of the present invention has substantially the same properties in all directions.

If membranes 40, 130, and 240 used in accordance with principles of the present invention are to remain on the application site for an extended period of time, such membrane preferably has a desired degree of breathability. Breathability may also be important for obtaining desired skin moisturization or proper skin moisture content balance for the functionality of the membrane in providing such benefit. Breathability relates to and is a function of oxygen exchange, which affects skin barrier as well as consumer perception. Breathability also is a function of water transmission. Membranes 40, 130, and 240 used in accordance with principles of the present invention preferably are sufficiently breathable so that the skin moisture content remains balanced. Of course, if one of the desired outcomes of use of the present invention is to improve or to increase skin moisture content, then the breathability of the membrane preferably may be selected to facilitate such moisturization, as discussed in further detail below. A semi-occlusive film will at least partially inhibit water loss and therefore hold moisture within the skin. Membranes 40, 130, and 240 used in accordance with principles of the present invention preferably provide resistance to moisture transmission, and may have a moisture transmission rate of approximately 50-150 grams of water per hour per square meter. Such membrane has been found to block or occlude evaporation that would occur without a film barrier by approximately 87%.

Membranes 40, 130, and 240 used in accordance with principles of the invention, as further described below, may be semi-occlusive (preferably approximately 50-85% occlusive) not only to maintain breathability, but also to provide other benefits discovered to result from covering the application site with a semi-occlusive membrane. In some embodiments, membranes 40, 130, and 240 of the present invention may comprise a top layer to further contribute to the overall semi-occlusive nature of the membrane. In particular, a top layer may function in conjunction with a hygroscopic skin-contacting layer. Once such a skin-contacting layer hydrates further, it may further lose structural integrity, and transform from a film-type substance to a gel phase without structural integrity independent of a top layer. The layer thus essentially caps and contains the skin-contacting surface at the application site so that the skin-contacting surface can hydrate the application site.

In some embodiments, membranes 40, 130, and 240 used in accordance with principles of the present invention dissolve or disintegrate with only the addition of water. Preferably, no mechanical agitation is required to facilitate the removal of the self-supporting adhesive film. Preferably, membranes 40, 130, and 240 used in the present invention preferably completely dissolves within the parameters of a typical consumer washing regimen for the application site if no membrane is present, so no additional washing time is required by the consumer. Preferably, membranes 40, 130, and 240 used in the present invention are quick-dissolving for ready removal from the application site on the user (when washing one's face, preferably less than about 5 minutes, and even less than about 1 minute, and even about 30 seconds after addition of a water thereto). It will be appreciated that a longer dissolution rate is acceptable for sites on other parts of the body that are typically washed for more than 5 minutes, but preferably not so long a dissolution time that scrubbing is required to achieve removal). With simulated cleansing water flow of about 4 feet/sec (parallel flow to surface of film), complete dissolution was measured in about 67 seconds with initial breach of the outer film surface occurring at about 30 seconds. In another embodiment, the membrane can be removed with a wet cloth, sheet, or pad made of woven or nonwoven materials.

The primary mechanical strength of the membrane is created by the film former (preferably polyvinyl alcohol (PVA)), which for membranes which breakdown with exposure to water, typically is also selected based on its ability to permit ready breakdown of the membrane as desired. It will be appreciated that in one embodiment, the film former preferably is selected to achieve the desired ability to dissolve or disintegrate the membrane for removal upon application of water thereto, and may be the first component of the membrane composition that is selected, other components being selected to interact as desired with the already-selected film former. Flexibility is achieved by the addition of a plasticizer, such as glycerin, to the film former. Film formers and/or plasticizers typically are the primary contributors to structural integrity, and are typically a component of the composition used to form the outwardly-facing top layer with properties such as described above. Exemplary film formers and plasticizers are set forth in greater detail below. Looking at solids content, PVA can be 70% by weight of the dry ingredients of a film structure used in accordance with principles of the present invention, with glycerin at 20% by weight. The glycerin can range from as little as 10% to 30% by weight of the film structure, and the PVA can be as much as 90% by weight of the dry ingredients.

Some hydrophilic film-forming polymers suitable for producing the topical skin membranes 40, 130, and 240 used in the present invention may be of synthetic, semisynthetic, or natural origin. Such hydrophilic film forming polymers include, without limitation, cellulose ethers, polyvinyl alcohols, polyvinyl acetate, polyvinyl pyrrolidone, polysaccharides, as well as derivatives, copolymers or polymers thereof. The multi-layer topical skin membrane may be made into a wide variety of product forms that include but are not limited to the form films.

The membranes 40 and 240, as well as the active regions 140 of the present invention contain at least one active substance, active agent, or benefit agent. The benefit agents that may be used in film structures of the invention include cosmetic agents and therapeutic agents. Such substances may be any of a variety of compositions, including, without limitation, hyaluronic acid; hydroxyl acids (e.g., glycolic acid, lactic acid, malic acid, salicylic acid, citric acid, tartaric acid); anti-acne agents (e.g., salicylic acid, retinol, retinoids, or other keratolytics, and benzoyl peroxide, or other antimicrobial agents used to treat acne); shine control agents (e.g., rice protein, cotton powder, elubiol (dichlorophenylimidazoltioxolan); a retinoid or its derivative such as tretinoin, isotretinoin, motretinide, adapalene, tazarotene, azelaic acid, and retinol; a 5-alpha-reductase inhibitor of amino acids, e.g., glycine derivatives; hydrolyzed vegetable proteins, including soy protein and wheat protein, etc.; green tea (*camellia sinesis*) extract, and cinnamon bark extract); moisturizers; anti-microbial agents (e.g., cationic antimicrobials such as benzylkonium chloride, benzethonium chloride, triclocarbon, polyhexamethylene biguanide, cetylpyridium chloride, methyl and benzothonium chloride; salts of chlorhexidine, such as Iodopropynyl butylcarbamate, diazolidinyl urea, chlorhexidene digluconate, chlorhexidene acetate, chlorhexidine isethionate, and chlorhexidene hydrochloride; halogenated phenolic compounds, such as 2,4,4'-trichloro-2-hydroxy diphenyl ether (Triclosan); parachlorometa xylenol (PCMX); short chain alcohols, such as ethanol, propanol, and the like); antibiotics or antiseptics (mupirocin, neomycin sulfate bacitracin, polymyxin B, 1-ofloxacin, tetracyclines (chlortetracycline hydrochloride, oxytetracycline-10 hydrochloride and tetracycline hydrochloride), clindamycin phosphate, gentamicin sulfate, metronidazole, hexylresorcinol, methylbenzethonium chloride, phenol, quaternary ammonium compounds, tea tree oil, and their pharmaceutically acceptable salts and prodrugs), anti-inflammatory agents (e.g., suitable steroidal anti-inflammatory agents such as corticosteroids such as hydrocortisone, hydroxyl triamcinolone alpha methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinol one acetonide, fluocinonide, flucortine butyl ester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and salts, non-steroidal anti-inflammatory agents, feverfew (*Tanacetum parthenium*), goji berry (*Lycium barbarum*), milk thistle extract (*Silybum marianum*), amaranth oil (*Amaranthus cruentus*), pomegranate (*Punica granatum*), yerbe mate (*Ilex paraguariensis* leaf extract), white lily flower extract (*Lilium Candidum*), olive leaf extract (*Olea europaea*) and phloretin (apple extract)); anti-mycotic/antifungal agents (e.g., miconazole, econazole, ketoconazole, sertaconazole, itraconazole, fluconazole, voriconazole, clioquinol, bifoconazole, terconazole, butoconazole, tioconazole, oxiconazole, sulconazole, saperconazole, clotrimazole, undecylenic acid, haloprogin, butenafine, tolnaftate, nystatin, ciclopirox olamine, terbinafine, amorolfine, naftifine, elubiol, griseofulvin, and their pharmaceutically acceptable salts and prodrugs; an azole, an allylamine, or a mixture thereof); external analgesics (e.g., ibuprofen- or diclofenac; capsaicin, fentanyl, and salts thereof such fentanyl citrate; paracetamol (as acetaminophen); non-steroidal anti-inflammatory drugs (NSAIDs) such as salicylates; opioid drugs such as morphine and oxycodone; ibuprofen- or diclofenac-containing gel); anti-oxidants (e.g., sulfhydryl compounds and their derivatives (e.g., sodium metabisulfite and N-acetyl cysteine), lipoic acid and dihydrolipoic acid, resveratrol, lactoferrin; ascorbic acid, ascorbic acid esters, and ascorbic acid derivatives (e.g., ascorbyl palmitate and ascorbyl polypeptide); butylhydroxy anisole, butylated hydroxytoluene (butylhydroxy toluene), retinoids (e.g., retinol and retinyl palmitate), tocopherols (e.g., tocopherol acetate), tocotrienols, and ubiquinone; cysteine, N-acetylcysteine, sodium bisulfite, sodium metabisulfite, sodium formaldehydesulfoxylate, acetone sodium bisulfite, tocopherols, and nordihydroguaiaretic acid; extracts containing flavonoids and isoflavonoids and their derivatives (e.g., genistein and diadzein); extracts containing resveratrol and the like; grape seed, green tea, pine bark, and propolis; plant-derived polyphenol antioxidants such as clove, cinnamon, oregano, turmeric, cumin, parsley, basil, curry powder, mustard seed, ginger, pepper, chili powder, paprika, garlic, coriander, onion and cardamom; typical herbs such as sage, thyme, marjoram, tarragon, peppermint, oregano, savory, basil and dill weed)); depilatory agents (e.g., calcium thioglycolate or potassium thioglycolate); vitamins (e.g., Vitamin A, Vitamin B, Vitamins C, Vitamin E; either alpha, beta, gamma or delta tocopherols, niacin or niacinamide) and vitamin salts or derivatives such as ascorbic acid diglucoside and vitamin E acetate or palmitate; sunblock (e.g., titanium dioxide) and/or sunscreen (e.g., inorganic sunscreens such as titanium dioxide and zinc oxide; organic sunscreens such as octylmethoxy cinnamates, octyl salicylate, homosalate, avobenzone); vasodilators (e.g., niacin); humectants (e.g., glycerin); anti-aging agents (e.g., retinoids; dimethylaminoathanol (DMAE), copper containing peptides); alpha hydroxy acids or fruit acids and their precursors such as glycolic acid, citric acid, lactic acid, malic acid, mandelic acid, ascorbic acid, alpha-hydroxybutyric acid, alpha-hydroxyisobutyric acid, alphahydroxyisocaproic acid, atrrolactic acid, alpha-hydroxyisovaleric acid, ethyl pyruvate, galacturonic acid, glucoheptonic acid, glucoheptono 1,4-lactone, gluconic acid, gluconolactone, glucuronic acid, glucuronolactone, isopropyl pyruvate, methyl pyruvate, mucic acid, pyruvic acid, saccharic acid, saccaric acid 1,4-lactone, tartaric acid, and tartronic acid; beta hydroxy acids such as beta-hydroxybutyric acid, beta-phenyl-lactic acid, and beta-phenylpyruvic acid; zinc and zinc containing compounds such as zinc oxides; botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, nice, and safflower, and salts and prodrugs thereof); carotenoids, ceramides, fatty acids, enzymes, enzyme inhibitors, minerals, steroids, peptides, amino acids, botanical extracts, colorants, etc. The substances may affect the skin in any of a variety of manners, such as by moisturizing; enhancing skin tone or color (such as with pigments); treating or at least mitigating various skin conditions (such as dry or severe dry skin, eczema, psoriasis, atopic dermatitis, allergic rashes, acne, blackheads, pustules, comedones, rosacea, shingles, wrinkles, cold sores, herpes, corns, warts, sunburn, insect bites, poison ivy, etc.); applying a mechanical force (such as shrinkage) to smooth wrinkles; or, more generally, treating or mitigating the symptoms and appearance of undesired skin imperfections (such as under eye dark circle, redness of acne, fine lines and wrinkles, post inflammatory hyperpigmentation (PIH), redness, inflammation, cellulite, wrinkles, age spots, mottled pigmentation, dark spots, liver spots, under eye puffiness); removing unwanted facial or body hair; aiding in wound healing; etc. For instance, lotions, creams, oils, and even masks may be applied to skin to treat or otherwise to affect the skin. Such personal or consumer healthcare substances are absorbed into the skin generally following the principles of diffusion, under which the rate of diffusion or transport across the skin is correlated with the difference in active concentration on both sides of the skin.

Method of Making the System

A system and method are also provided that comprise at least (a) an imaging device system that capture user's digital face geometry and images of face condition for skin analysis, and feeds its outputs to a center computer system comprising a connection center, cloud based-hub computing data system where the digital data of user's face geometry and images of face condition can be uploaded, stored and shared, (b) a 2D to 3D reconstruction and artificial intelligent (machine learning) algorithms for geometry and appearance reconstruction, (c) a skin feature database for skin comparison and grading, (d) skin analysis algorithms that provide skin analysis output images, face maps, evaluation results and treatment recommendations to user, (e) an internet portal site provided for user access for inputs and treatment selections. Outputs from the central computer system are provided for download to local computer, treatment formulator, and 3D printing or digital computational thermo-vacuum former and 6-axis robot treatment-deposition device which deposit various treatments onto membrane to face of mask body to generate a personalized conformal facial mask with area-specific personalized treatment for that particular user. Similar approach can be applied to individual patch or a group of patches.

Method of Using the System

In addition we have identified a method for targeted application of topical agents to an isolated body part comprising the steps of capturing an image of the isolated body part, transforming the image data to mathematical model of the geometry of the isolated body part, forming an applicator mask having an applicator surface having a three dimensional shape corresponding to the isolated body part, forming a releasable membrane on the applicator surface of the applicator mask comprising one or more benefit agents disposed in one or more treatment zones of the applicator, where the adhesion of the membrane to the isolated body part is greater than the adhesion of the membrane to the applicator surface, disposing the applicator mask on the isolated body part so that the releasable membrane is in contact with the isolated body part, and removing the applicator mask from the isolated body part so that the membrane remains in contact with the isolated body part.

In use, a system scans a patient's body part positioned in the field of scan, and being scanned by an imaging device. This imaging device is capable of sensing many characteristics (shapes and micro geometries) from the patient's body part. For instance, device may sense local body geometry shape with white light (LED), infrared emissions from area of increased heat, reflectivity sensing oiliness or dryness of skin, and local body defects (micro-geometry) such as spots, wrinkles, blemishes, texture, pores, UV spots, brown spots red areas, porphyrins, acne, etc. with different light sources, for example, commercial available image device VISIA, VISIONFACE 1000D, Sony Beauty Explorer, and the like. These characteristics are merely exemplary a preferred embodiment, however, it is to be appreciated that such examples are not intended to limit the functionality of imaging device as any imaging device known in the art is fully contemplated herein.

The imaging device provides an output which is in electrical communication to a central computer system where the computer software and associated computing device is programmed to process the data and generate a customized skin profile for that individual user showing various skin conditions and corresponding locations of skin conditions in the captured images. The system is also programmed to generate recommendations for treatment of various skin conditions identified in the skin profile. All the data captured from user will be output to a center computer system comprising a connection center, cloud based-hub computing data system where the digital data of user's face geometry and images of face skin condition can be uploaded, stored and shared for downstream process.

For example, commercially available imaging devices that can be used for capturing local body shape in the present invention include, for example, Digital 3D scanner Go!scan20™ from CREAFORM, ISENSE from 3D system, ARTEC SPIDER, NIKON MODELMAKER MMCx, OPTIX 5005 form 3D Digital CORP, etc.

For instance, the face image of the present invention may be captured with digital 3D scanner such as Go!scan20™, or with high end digital camera or video camera, or just a consumer grade camera, such as, for example, a cell phone through 2D to 3D reconstruction software algorithm. Preferably, more than one image of the user is captured, each from a different angle such that an analysis can be accomplished, for example, of the entire face. Along with the images, positioning information is acquired with respect to the captured images. The acquired positioning information on the images may be analyzed to determine surface topography for mapping local body defect area or treatment areas.

In one embodiment of the present invention a 3D model of the anatomically customized mask is created using multidimensional data from an individual's face. The data may be acquired through 3D scanner, multiple image or video cameras and digital 2D to 3D reconstruction software, point cloud or triangulate scans from digital image scanners, or any number of 3D modeling technologies. Once the digital data of the individual face 3D surface captured in the system, software in the system may further customize the mask applicator 20 to provide automatically rendering, cleaning scan noise and enhanced functionally aesthetics.

Digital 3D images of entire face, for example, captured with digital 3D scanner Go! Scan20™ can be formatted and digitally stored in central computer system where computer software Geomagic Design X from 3D system provide 3D rendering and cleaning noise of the 3D scanned data, and associated software (e.g., Solidworks or Inventor) is programmed to process the 3D rendering data and generate a 3D model for applicator 20. The 3D model then can be downloading to 3D printer to print the applicator 20 by utilizing plastic thermoset material or plastic materials.

One the example of the present invention provides a customized mask applicator formed utilizing 3D printing technologies for conforming to the unique facial features of the user. The mask applicator 20 embodiments of the present invention are customizable for each user to provide matching contours of the human face for increased comfort when the mask is worn.

Since 3D printing technology is used in the present invention, any digitized model must be mathematically translated into 3D printable format of the desired print-out. Importantly, to ensure customized fit of the face mask, the customized, contoured facial mask applicator face portion, is constructed and configured to cover and to contact a corresponding contoured surface area of human face, is unitarily and integrally formed by 3D printing technology, and is formed of non-toxic synthetic material, thermoset plastic or plastic. Preferably, a soft plastic layer or rubberlike layer is provided on the surface that contacts the face of user. For example, commercial available 3D printing technology such as Fused deposition modeling (FDM), Fused filament fabrication (FFF), Stereo lithography (SLA), Digital Light Processing (DLP), Powder bed and inkjet head 3D printing (3DP) Selective heat sintering (SHS), and Selective Laser sintering (SLS) can be utilized to form applicator 20 with different type of thermoplastic, thermoplastic powders, and thermoset photopolymer. For example, applicators in the present invention can be formed by utilizing Stratasys Connex 3 3D printer with so called digital materials (include primary material: TANGOPLUS FLX930 and secondary material: VEROCLEAR RDG 810, or VEROWHITEPLUS RGD835) controlled with different layer's softness between 35 to 95 Shore Hardness (A).

Applicator 20 then can be physically transferred to 6-axis robot treatment-deposition device which deposit prefer benefit agents on to second surface 24 of applicator 20.

EXAMPLES

The present invention will be further understood by reference to the following specific example that is illustrative of the composition, form and method of producing the device of the present invention Example 1: Formation of Skin Treatment System 200

With reference to FIGS. 8-9, a user with the desire to treat acne in several regions of her face uses an imaging device system to capture her digital face geometry as well as images of face condition for skin analysis. The image output is sent to a center computer system comprising a connection center, cloud based-hub computing data system where the digital data of her face geometry and images of face condition can be uploaded, stored and shared with a mask forming system. The face forming system creates an individualized skin treatment system 200, in the form of an acne treatment facial mask for the user.

Skin treatment system 200 includes applicator 220 having a first surface 222, and a second surface 224. Applicator 220, comprised of poly(ethylene) is formed using a thermo-vacuum former (Formech thermos-vacuum former machine 300XQ) with a mold cavity in the shape of a human face, at conditions required to mold the PE into the face-mask shape. The temperature is about 260° F. to about 360° F., and the vacuum is between about 750 mbar to about 914 mbar). Alternatively, the applicator 220 is formed using a Stratasys 3D printer Connex 3X and Objet 24 with model material VEROWHITEPLUS RGD835 and support material Sup705 (temperature 73° C. for both material during 3D printing process).

Second surface 224 of applicator 220 is treated with a release agent such as a cross-linkable silicone solution. Membrane 230 is disposed on second surface 224 of applicator 220 using a 6-axis robot treatment-deposition device, such as a DENSO Model: VP-6242E/GM device.

Table 1 shows several formulations which are used to form membrane 230.

TABLE 1

| Compositions for membrane 230 (wt %). | | | | |
|---|---|---|---|---|
| Ingredients | 230A | 230B | 230C | 230D |
| Selvol 805 | 16.86 | 16.86 | 16.86 | 16.86 |
| Vitacel Oat Fiber HF600-30 | 11.82 | 11.82 | 11.82 | 11.82 |
| Salicyclic Acid, USP, Powder | 1.14 | 1.25 | 1.02 | 1.06 |
| Polysorbate 80 | 1.80 | 1.80 | 1.80 | 1.8 |
| Dow Corning 2501 Cosmetic Wax | 1.24 | 1.24 | 1.24 | 1.24 |
| Kester Wax K-24 | 1.24 | 1.24 | 1.24 | 1.24 |
| Glycerin 99.7%, USP | 10.30 | 10.30 | 10.30 | 10.3 |
| Lactic Acid, Ritalac LA | 5.61 | 5.61 | 5.61 | 5.61 |
| Water, Purified | 50.00 | 49.89 | 50.11 | 50.07 |
| TOTAL (wt %) | 100.00 | 100.00 | 100.00 | 100.00 |

Membrane 230 has a first surface 232, and a second surface 234. Active regions 240a, 240b, 240c, and 240d which contain the acne treatment benefit agents, are formed using a 6-axis robot treatment-deposition device. Table 2 shows several formulations which are used to form active regions 240.

TABLE 2

| Compositions for active regions 240 (wt %). | | | | |
|---|---|---|---|---|
| Ingredients | 240A | 240B | 240C | 240D |
| Plasdone S-630 | 28.19 | 28.19 | 28.19 | 28.19 |
| Polyox WSR N-10 | 6.40 | 6.40 | 6.40 | 6.4 |
| Vitacel Oat Fiber HF600-30 | 6.98 | 6.98 | 6.98 | 6.98 |
| Glycerox 767 | 1.16 | 1.16 | 1.16 | 1.16 |
| Salicyclic Acid, USP, Powder | 1.14 | 1.25 | 1.02 | 1.06 |

TABLE 2-continued

Compositions for active regions 240 (wt %).

| Ingredients | 240A | 240B | 240C | 240D |
|---|---|---|---|---|
| Monomuls 90-O18 | 2.93 | 2.93 | 2.93 | 2.93 |
| Aquacoat ECD, Ethylcellulose Dispersion (30%) | 9.75 | 9.75 | 9.75 | 9.75 |
| Feverfew | 1.37 | 1.37 | 1.37 | 1.37 |
| Water, Purified | 42.07 | 41.96 | 42.19 | 42.16 |
| TOTAL wt % | 100.00 | 100.00 | 100.00 | 100.00 |

The membrane is then transferable from the applicator to the user's isolated body part. After a desired treatment time, the membrane may be removed from the user with a soap and water wash.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A method for targeted application of topical agents to an isolated body part comprising the steps of:
   (a) capturing an image of the isolated body part;
   (b) transforming the image data to mathematical model of the geometry of the isolated body part;
   (c) forming an applicator mask having an applicator surface having a three-dimensional shape configured to cover and to contact a corresponding to contoured surface area of the isolated body part;
   (d) forming a plurality of releasable membranes in a stack on the applicator surface of the applicator mask from a releasable membrane adhered to the applicator surface to an exposed releasable membrane, each releasable membrane comprising one or more benefit agents disposed in one or more treatment zones of the applicator, wherein the releasable membranes are pre-configured to cover and contact the contoured surface of the isolated body part and the adhesion of the exposed releasable membrane to the isolated body part is greater than the adhesion of the first releasable membrane to the applicator surface and to a membrane disposed adjacent to the exposed releasable membrane in the stack;
   (e) disposing the applicator mask on the isolated body part so that the exposed releasable membrane is in contact with the isolated body part without substantial deformation of the exposed releasable membrane; and
   (f) removing the applicator mask from the isolated body part while leaving the exposed releasable membrane in contact with the isolated body part.

2. The method of claim 1, wherein the steps of forming an applicator mask and forming a releasable membrane are performed utilizing 3D printing.

3. The method of claim 1, wherein the step of forming an applicator mask comprises thermo-vacuum forming.

4. The method of claim 3, wherein the step of forming a releasable membrane comprises applying one or more film-forming compositions to the applicator mask via a robot treatment-deposition device.

5. The method of claim 4, further comprising applying a plurality of film forming compositions, at least one of the plurality of film-forming compositions comprising the one or more benefit agents.

* * * * *